United States Patent [19]
Bogentoft et al.

[11] Patent Number: 5,492,937
[45] Date of Patent: Feb. 20, 1996

[54] GEL-FORMING LIQUID CARRIER COMPOSITION

[75] Inventors: Conny Bogentoft, Vällingby; Anders Carlsson, Stockholm, both of Sweden

[73] Assignee: Pharmacia AB, Sweden

[21] Appl. No.: 64,141

[22] PCT Filed: Oct. 30, 1991

[86] PCT No.: PCT/SE91/00731

§ 371 Date: May 21, 1993

§ 102(e) Date: May 21, 1993

[87] PCT Pub. No.: WO92/09307

PCT Pub. Date: Jun. 11, 1992

[30] Foreign Application Priority Data

Nov. 22, 1990 [SE] Sweden ................................. 9003712

[51] Int. Cl.⁶ ............................................... A61K 47/38
[52] U.S. Cl. .................. 514/781; 514/944; 424/426; 424/428; 424/430; 424/434; 424/435; 424/436; 424/437; 424/445
[58] Field of Search ....................... 424/488, 423, 424/426, 427, 428, 430, 434, 435, 436, 443, 444, 446, 450, 781; 514/944; 536/87, 88, 90, 91, 95, 96, 99, 100

[56] References Cited

U.S. PATENT DOCUMENTS

| | | | |
|---|---|---|---|
| 4,042,719 | 8/1977 | Zimmermann et al. | 426/573 |
| 4,474,751 | 10/1984 | Haslam et al. | 514/11 |
| 4,474,752 | 10/1984 | Haslam et al. | 434/78 |
| 4,474,753 | 10/1984 | Haslam et al. | 424/78.06 |
| 4,478,822 | 10/1984 | Haslam et al. | 424/94.6 |

FOREIGN PATENT DOCUMENTS

| | | |
|---|---|---|
| 0529401 | 9/1956 | Canada. |
| 0157695 | 9/1985 | European Pat. Off.. |
| 0157695A3 | 10/1985 | European Pat. Off.. |
| 0323510A1 | 7/1989 | European Pat. Off.. |
| 0386960A2 | 9/1990 | European Pat. Off.. |
| WO89/11503 | 11/1989 | WIPO. |

OTHER PUBLICATIONS

63–Pharmaceuticals, vol. 97, 1982, p. 413. Chem. Abstracts.

Primary Examiner—Carlos A. Azouru
Attorney, Agent, or Firm—Pollock, Vande Sande & Priddy

[57] ABSTRACT

A carrier composition that is a liquid at or below room temperature forms a high viscosity layer or gel at body temperature, which comprises a water-soluble, nonionic cellulose ether having a cloud point not higher than 40° C., a charged surfactant and optional additives in water. The carrier composition can be used for oral or local administration of a pharmacologically active substance to the skin, mucous membrane, the eye or a body cavity.

20 Claims, 2 Drawing Sheets

GEL-FORMING LIQUID CARRIER COMPOSITION

The present invention refers to a carrier composition which is liquid at or below room temperature and forms a high viscosity layer or gel at body temperature. The invention also refers to a pharmaceutical composition containing a pharmacologically active substance in combination with said carrier composition. Said compositions can be orally or locally administrated to the skin, the mucous membrane, the eye or a body cavity.

For local administration of a drug to different regions of the human body in order to obtain a local or systemic pharmacological effect the drug is normally combined with a semi-solid or liquid carrier to optimize drug uptake and administration. For many non-parental routes of administration there is often a need to prolong the duration of residence of the dosage form. This can be achieved by using a bioadhesive system, wherein the dosage form, by virtue of containing a bioadhesive polymer, adheres to the skin or the mucosa until the polymer dissolves or is replaced.

Polymers having bioadhesive properties are for instance water-soluble cellulose derivatives, such as sodium carboxymethyl cellulose, and polyacrylic acids, which are used in many pharmaceutical preparations to improve the contact between drug and body. If these polymers are administrated in liquid form they are, however, removed too fast. If a solid or viscous dosage form is used for local administration of drugs, there will on the other hand be limitations in the routes of administration and use in clinical practice.

Ophthalmic drugs delivered topically to the eye commonly have a low bioavailability. Rapid loss of the instilled drug via drainage through the drainage apparatus has a considerable influence. This loss leads to a short contact time between drug and cornea, making the drug less available for absorption into the eye. A well-known approach to improve the bioavailability of topically applied drugs is to prolong their corneal contact time. Improved uptake has been achieved by using vehicles containing viscosity-increasing polymers such as the cellulose derivatives, polyvinyl alcohol and polyvinylpyrrolidone. It is postulated that the increased viscosity results in reduced drainage of the instilled preparation, thereby increasing the bioavailability of the drug.

Thermogelling pharmaceutical preparations are described in for instance U.S. Pat. Nos. 4,478,822, 4,474,751, 4,474,752 and 4,474,753. Said patents refer to a drug delivery system which at room temperature has the properties of a liquid, but forms a semi-solid gel at human body temperatures. The compositions to be administered comprise 10 to 50% by weight of a polymer, which is a tetra-substituted derivative of certain diamines containing approximately 40 to 80% poly(oxyethylene) and approximately 20 to 60% poly(oxypropylene), as a drug delivery vehicle. In this system the gel transition temperature and/or the rigidity of the gel can be modified by adjustment of the pH.

Other systems are known in which the gelling is induced by an increase in the amount of electrolytes or a change in pH.

It has now surprisingly been found that certain water-soluble nonionic cellulose ethers in combination with a charged surfactant and optional additives in water have the property of being liquid at room temperature and forming a gel when warmed to body temperature. The process is reversible. These cellulose ethers also have been shown to have excellent bioadhesive properties. Such characteristics can be utilized for specialized drug delivery. The drug can be introduced on or into the body as a solution which will gel and adhere to body tissue just by means of the raise in temperature—no pH gradients or high electrolyte contents are required for the gelling.

The carrier composition of the invention is characterized in comprising a water-soluble, nonionic cellulose ether having a cloud point not higher than 40° C., preferably not higher than 35° C., a charged surfactant, and optional additives in water.

The carrier composition of the invention is also characterized in comprising a very low polymer concentration, that is the combined concentration of the cellulose ether and the surfactant is below 3% by weight, and preferably 0.5–1.5% by weight.

BEST AND VARIOUS MODES FOR CARRYING OUT INVENTION

Figure 1:
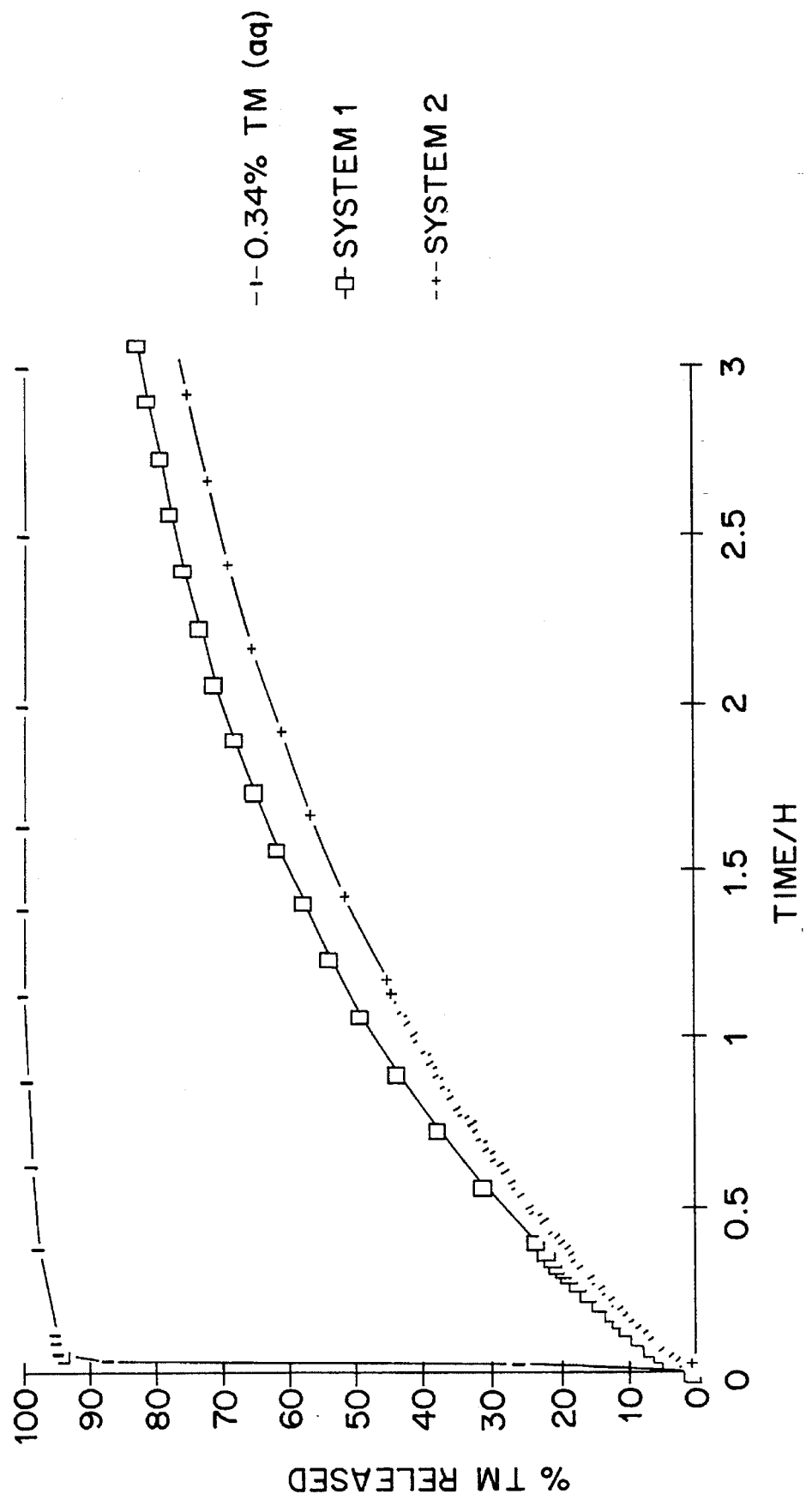
FIG. 1 is a graph demonstrating release rate of timolol maleate from different carrier systems.

The nonionic cellulose ethers in the composition of the invention are based on cellulose which has been chemically modified in order to attain solubility in water by substitution of various groups onto the cellulose backbone. The types and numbers of substituents should be chosen in such a way as to give the cellulose ether a limited solubility with respect to temperature increases. Thus aqueous solutions of the cellulose ethers have a particular temperature above which a two-phase system is formed, which initially causes a strong light scattering and thus the system has a cloudy appearance—this temperature is commonly referred to as the cloud point (CP) temperature.

Cloud point (CP) temperatures are determined on a Mettler FP5+FP51 spectrophotometer. The sample solution (1.0 wt % aqueous cellulose ether solution in a capillary tube) is heated at a rate of 10° C./min. The CP is then graphically determined as the break-point in the recorded absorbance-versus-time curve.

In order to be liquid at room temperature and gel at body temperature, that is about 37° C., the cellulose ethers should have a CP not higher than 35° C. If it is sufficient that a high viscosity layer is formed, the cloud point could be up to 40° C.

The properties of the cellulose ethers are determined by the type of substituents and also by their number and distribution along the molecule.

The most appropriate cellulose derivatives are nonionic, where alkyl and/or hydroxyalkyl groups are attached to the anhydroglucose units by ether linkages, that is alkyl hydroxyalkyl celluloses, wherein the alkyl groups have from 1 to 4 carbon atoms.

Representative cellulose ethers are methyl cellulose (MC), methyl hydroxyethyl cellulose (MHEC), methyl hydroxypropyl cellulose (MHPC), ethyl hydroxyethyl cellulose (EHEC), and hydroxypropyl cellulose (HPC). These polymers all have substituents that are either nonpolar (e.g. methyl) or slightly polar (e.g. hydroxyethyl), which in combination with the hydrophilic cellulose backbone give rise to an amphiphilic polymer.

A preferred cellulose ether is EHEC, having the chemical formula

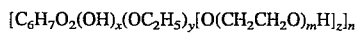

$$[C_6H_7O_2(OH)_x(OC_2H_5)_y[O(CH_2CH_2O)_mH]_z]_n$$

where n is the degree of polymerisation, y is the degree of ethyl substitution ($DS_{ethyl}$), and (m+z) is the molar hydroxyethyl (ethylene oxide; EO) substitution ($MS_{EO}$). The average values of y and (m+z) could range from 1.2 to 2.5 and from 0.5 to 1.5, respectively; the actual values are dependent on n and the heterogeneity of substitution.

The substitution of EHEC is thus characterized by the values $DS_{ethyl}$ and $MS_{EO}$: the former value equals the average number of hydroxyl groups on the anhydroglucose unit which has been substituted by ethyl groups, whereas the latter corresponds to the average total number of ethylene oxide groups substituted on the anhydroglucose unit. Ethylene oxide (hydroxyethyl) can form short oligo(ethylene oxide) chains and thus $MS_{EO} > DS_{EO}$.

The molecular weight, i.e. the degree of polymerisation (n), of the cellulose ether seems to be less important for obtaining the gelling effect. This may be because all the employed solutions are semi-dilute, i.e. the cellulose ether concentrations considerably exceed the so-called overlap concentration.

A preferred EHEC to use in a composition of the invention is EHEC of medical grade (Berol Nobel, Sweden), that is ethyl hydroxyethyl cellulose ethers having a cloud point of 30°–35° C., especially 32°–35° C. These cellulose ethers normally have a $DS_{ethyl}$ of 1.2–2.5 and an $MS_{EO}$ of 0.5–1.5, but they may also contain minor amounts of other substituents, such as methyl and hydroxypropyl. The degree of polymerisation of said cellulose ether could be 200–600, preferably 500–600. The viscosity of said EHEC is 30–400 cP in a 1% aqueous solution as measured according to Brookfield LV, 12 rpm at 20° C. The medical grade EHEC is more hydrophobic than the grades of EHEC which are commercially available today.

Tests have shown that EHEC has bioadhesive properties both in the presence and absence of surfactants.

The present invention also refers to the use of an aqueous solution of ethyl hydroxyethyl cellulose having a $DS_{ethyl}$ value of 1.2–2.5, $MS_{EO}$ value of 0.5–1.5 and a cloud point of 30°–35° C. as a carrier for administration of a pharmacologically active substance.

Cellulose ethers are generally nontoxic and high purity grades of most commercial products are approved as food additives and for use in cosmetics as well as in pharmaceutical compositions.

The surfactant should contain either a positively or a negatively charged headgroup. Examples of the former surfactants are alkyl ammonium compounds (e.g. hexadecyltrimethylammonium, tetradecylbetainate and hexadecylpyridinium salts, e.g. chloride and bromide). Examples of the latter are alkyl sulphates (sodium dodecyl sulphate), alkyl ether sulphates (sodium dodecyl monoethyleneoxide sulphate), alkyl sulphonates (sodium dodecyl sulphonate), alkyl phosphates (sodium dodecyl phosphate), alkyl phosphonates (sodium dodecyl phosphonate), alkylarylsulphonates (sodium p-dodecylbenzene sulphonate) and salts of saturated or unsaturated fatty acids (potassium and sodium dodecanoate, tetradecanoate, hexadecanoate, octadecanoate, 9-hexadecenoate, cis-9-octadecenoate). The examples listed above normally contain a single hydrocarbon chain which should contain between 10 and 20 carbon atoms in order to interact strongly enough with the polymer. Other examples are amino acid and carbohydrate based surfactants, e.g. acyl glutamates and salts of acyl arginine esters (N-myristoyl-L-argine methyl ester, hydrochloride), and puranosyl glycerides, respectively.

It is also possible to use ionic double-chained surfactants and lipids with more than 8 carbons per chain, such as phospholipids (e.g. phosphatidylglycerols, phosphatidyl serins, and phosphatidyl inositols), dialkyl ammonium compounds, dipuranosyldiglycerides (e.g. digalactosyldiglyceride), and Aerosol OT (sodium bis(2-ethylhexyl)sulpho succinate).

The amount of surfactant is of the same order of magnitude as the critical micelle concentration in a polymer-free solution. The optimum concentration of the surfactant in the composition of the invention is in the order of 0.2–5 times the critical micelle concentration.

According to another aspect of the invention the charged surfactant can be an amphiphilic drug, an ionic drug derivatized with a hydrocarbon chain, saturated or unsaturated, of a length sufficient to cause the EHEC gel to form on temperature increase, or a lipophilic drug derivatized with an ionic group. The derivatized drug is by definition a prodrug. Depending on the nature of the prodrug it may be possible to control the fate of the gel after the prodrug has been converted into its corresponding parent drug. After the conversion and the release of the parent drug the remaining lipophilic part of the prodrug could be either charged in which case the gel is maintained, or noncharged, leading to the destruction of the gel. For example, if the prodrug consists of a long aliphatic chain connected to the parent drug via an ester bond, the hydrolysate could either consist of the drug and a dissociated fatty acid or the drug and a fatty alcohol.

By this the charged surfactant, which is only used to give a gel, and might not be desirable from a toxicological point of view, can be at least partly omitted. Other advantages with this system is that the release of drug can be better controlled; a combination of drug and prodrug can give a bolus and a prolonged effect; and that the drug might be better protected from degradation as being adsorbed to EHEC. This latter aspect might be important for instance in connection with propeptides and other prodrugs of macromolecules.

The origin of the gel formation is a strong hydrophobic interaction between polymer and surfactant which is cooperative in nature and thus resembles normal micelle formation. Surfactant clusters formed in this way may then act as cross-links between different polymer chains, giving rise to an extended three-dimensional gel structure. The electrostatic repulsion between different surfactant clusters may lead to polymer chain expansion which may also contribute to the increase in gelling/viscosity. Furthermore, and most importantly, the hydrophobic attraction between the two species has been shown to be promoted by an increase in temperature—a surprising experimental fact—explained as a result of increased hydrophobicity of the polymer upon heating. The whole process is reversible: on cooling, the system regains its original properties.

It is possible to control the gel formation, both the temperature at which maximum viscosity occurs and the strength of the gel, by different means. This is performed by varying the concentration of either the cellulose ether or the surfactant. Alternatively, the gel-forming strength could be altered by replacing the surfactant with another which binds either less or more strongly to the polymer. A more amphiphilic surfactant, reflected in having a longer alkyl chain and thus a lower critical micelle concentration, would bind more strongly to the polymer and give rise to a stronger gel on heating at a lower surfactant concentration than would be produced by a less amphiphilic surfactant.

The ratio of surfactant to cellulose ether should be 1:5 to 1:25 by weight. Generally this ratio is about 1:10. The total concentration of cellulose ether and surfactant in the composition is comparatively low, it should not exceed 3% by weight and preferably be from 0.5 to 1.5% by weight.

Once the gel is formed it is very resistant to the effects of high salt concentrations; actually, salt promotes the stability of the gel in different ways. Firstly, the adsorption of surfactants on to the polymer chain is favoured by the diminished electrostatic repulsion between charged headgroups caused by the added counterions; this leads to a decrease in the concentration of singly dispersed surfactant molecules. Secondly, a high salt content leads to a reduced solubility of the polymer reflected in increased interpolymer attractions; all in all, the three-dimensional network built-up by polymer chains and surfactant clusters is strengthened.

However, if salt is present in the polymer solution during the preparation e.g. in physiological concentrations, higher surfactant concentrations are necessary.

In accordance with a specific embodiment of the invention the carrier composition, especially for oral administration also comprises a nonionic, low-molecular compound in an effective isotonic concentration, such as sucrose, glucose, glycerol. This produces an isotonic gel which does not undergo shrinkage in a physiological medium.

The carrier composition can in addition contain optional additives known in the art for improving different aspects of the composition, such as flavouring agents, colorants and preservatives.

At, or below, room temperature, the carrier composition, e.g. a water-based EHEC-surfactant system, is a clear, low-viscous aqueous solution without unpleasant taste and smell. The water content could be as high as 99 wt %, which means that the carrier composition is easy to drink, instil or spray.

The carrier of the invention can be used for oral or local administration of a drug or a prodrug to the skin, the mucosa, the eye or a body cavity such as the mouth, ear, nose, vagina, rectum.

The liquid carrier system has a viscosity that allows spraying, instilling, pouring, drinking or spreading the dosage form into the intended biological cavity or part of the body. Upon administration the liquid carrier composition will adhere to the mucus or the biological membrane and form a high viscosity or gel layer.

Tests in vitro as well as in vive have shown that the composition of the invention gels in gastric juice and that this gel is also retained in intestinal juice. This implies that on oral administration of a drug in a carrier of the invention a gel will form in the gastrointestinal tract giving a slow release of the active substance, as well as an improved bioavailability. In order for a gel to form in the gut a cationic surfactant or an anionic surfactant not being protonized at low pH should be used. An anti-asthma drug, such as theofylline, may then be incorporated without affecting the gelling mechanism. Once the gel is formed it is very resistant against salt and mechanical rupture and the gastric emptying time will be prolonged. The diffusion of the drug within the gel lump is normally not restricted (except for drugs having a charge opposite to the surfactant)—instead the border between low salt (gel) and high salt (physiological medium) serves a diffusion barrier.

The inherent bio(muco)adhesive properties of EHEC makes it suitable as a constituent in saliva substitutes.

Objective (friction measurements) and subjective (questionnaire) efficacy evaluations of EHEC solutions with and without ionic surfactant on patients suffering from xerostomia have been performed. It was established that EHEC solutions relieve the symptoms of mouth dryness, with good lubricating properties. This is explained as a result of the high water-retaining capacity and gel-like structure of the EHEC system.

Mucoadhesion studies in vitro (detachment force measurements) have shown that both EHEC solutions and EHEC-ionic surfactant solutions adhere strongly to a model mucus gel at 37° C.

If the mouth rinse solution contains a suitable anionic surfactant it is possible to incorporate fluoride ions ($F^-$) for anticaries treatment. The fluoride content (as NaF) could vary between 0.05 and 0.2 wt % without affecting the gelling behaviour significantly if sodium dodecyl sulphate (SDS) is used. After being warmed up in the mouth the solution is transformed to a gel which sticks to the mucous membrane in a thin layer. The gel could then provide a source of $F^-$ ions which are slowly released to the saliva.

The ideal product will have a low viscosity at room temperature so that it can easily be taken orally. At mouth temperature the product should become viscous, thus sticking to the palate and gum. However, it should not gel in the mouth, in order to have a high-patient compliance.

When used to treat conditions of the eye, nose or ear the liquid carrier may be administered by any conventional means of delivering drop formulations.

Adding an ionic surfactant to a nonionic cellulose ether solution improves the carrier from a bioavailability point of view. The surfactant modifies the carrier in that it undergoes a temperature dependent transformation from a low viscous solution to a solution with higher viscosity, but still retains its pseudoplastic behaviour. This means that at room temperature the solution is easy to administer as eye drops since the solution has low viscosity and in contact with the eye (35° C.) will become more gel-like in consistency. The surfactant decreases the surface tension of the polymer solution and accordingly the size of administered drops from an eyedrop bottle. This is also an advantage since numerous studies have shown that the precorneal drainage rate of solutions in the eye increases linearly with instilled volume. In other words, reduction of the instilled volume increases ocular drug availability.

EHEC shows several advantages over other polymers proposed as ocular vehicles, where increased viscosity is dependent on external factors, such as pH and electrolytes.

Tranexamic acid, used as a haemostatic agent, could be dissolved in an EHEC-surfactant solution to give a highly viscous one-phase system. Typical concentrations of tranexamic acid and EHEC-surfactant are 10 and 1 wt %, respectively, which result in an isotonic solution having an appropriate pH of 7. One dose in each nasal cavity (2×100 μl) would then correspond to 20 mg tranexamic acid. After being applied in a drop, either by using a single unit dose pack or a pipette, the solution stiffens which thereby prolongs the action of the drug. The same principle of mixing tranexamic acid with EHEC-surfactant solution could be used for any local haemostatic treatment, e.g. gastric or colonic ulcer.

Polypeptides and polysaccharides could also be administered by means of the EHEC thermogel vehicle. Nasal delivery of insulin may serve as an example. EHEC-surfactant formulations, containing therapeutic relevant concentrations of insulin, improve the absorption of insulin due to the increased contact time between mucus and the drug. This has been established by measurements of the blood glucose level in rats. Furthermore, release profiles in vitro confirm that also macromolecules could be efficiently sustained when using the thermogel system based on EHEC and ionic surfactant. The role of the surfactant is, besides taking part in the gel structure, to enhance the penetration of drug through the mucous membrane. Another advantage of this system is the fact that the gel does not undergo phase separation as other thermoreversible polymer systems do. The ability of the EHEC-surfactant gel to maintain its water content after being applied may facilitate the penetration.

When used for rectal, urethral or vaginal administration, the liquid carrier is administered by any conventional means, e.g. a syringe.

The bioadhesion properties will make the drug stay in contact with the tissue for a longer time.

Local administration can be made to serve the purpose of enhanced systemic absorption. One goal could be to avoid first pass metabolism.

The drug release can be controlled within certain limits to permit a more even blood concentration level. It can make it possible to reduce the number of administrations and increase compliance.

The pharmaceutical composition of the invention which is a liquid at and below room temperature and forms a high viscosity layer or gel at body temperature comprises a pharmacologically active substance in combination with a carrier composition as described above.

Any pharmacologically active material which is water-soluble may be delivered in the drug delivery system of this invention. Preferably the drug is noncharged. Salts of a drug could also be used even if this may require higher surfactant concentrations. In this respect it may be more advantageous to use the noncharged form, e.g. the base form of an amine-containing drug instead of its corresponding salt, provided the base is soluble in water.

If incorporating a salt, regardless of being organic or inorganic, an upper limit in concentration exists. High salt concentrations during the mixing procedure lead to precipitation of the liquid drug carrier which thus limits its applicability to high drug loading. However, the increased contact time and improved drug uptake from the liquid drug carrier compared with an aqueous solution means that a lower drug concentration could be used.

The drug may also be insoluble in water and can be suspended in the drug delivery system. Both the polymer and the surfactant are amphiphilic in nature and adsorb on to solid particles and alone protect from sedimentation. The present invention provides an even better stabilizing effect when finely ground particles are suspended since the carrier system is a combination of polymer and ionic surfactant.

According to a specific embodiment of the pharmaceutical composition the charged surfactant could be replaced, in part or in total, by an amphiphilic drug.

The preparation of the liquid drug carrier is described below and the appropriate examples which follow were all performed according to this procedure. The polymeric component of the liquid carrier system dissolves better at low temperatures and thus the polymer is dispersed in warm water to avoid lump formation and then preferably put in a cold place, such as a refrigerator or thermostated container. The mixture should be stirred to facilitate the dissolution of the polymer. The whole procedure is completed within 2 h but normally the solution is aged overnight in a cold place. The second component of the liquid carrier, the ionic surfactant is then added in appropriate amounts, generally in a ratio of surfactant to polymer of about 1:10 by weight.

The drug substance and various additives such as preservatives and nonionic, low-molecular compounds in an effective isotonic concentration are then added.

Drugs which can be administered in the drug delivery system of the present invention are antibacterial substances such as p-aminosalicylic acid, N-formamidoyl thienamycin, penicillin, tetracycline, chloramphenicol, neomycin, bacitracin, and the like; sulfamethazine, sulfanilic acid, sulfaphenazole, sulfasymazine, sulfamoxole, sulfamipyrine and the like;

aminoglycoside antibiotics such as gentamycin, kanamycin, amikacin, sisomicin and tobramycin and the like; norfloxacin and the like;

antihistaminics and decongestants such as pyrilamine, pheniramine maleate, zolamine, antazoline and the like;

anti-inflammatory substances such as corticosteorids, such as cortisone, hydrocortisone, hydrocortisone sodium succinate, hydrocortisone sodium phosphate, prednisolon, methylprednisolon, triamcinolon, dexamethasone, budesonide; phenybutazone, ibuprofen, indomethacin and its salts, sulindac, allopurinol, oxyphenbutazone and the like;

various peptide hormones such as insulin, somatostatin and analogues of those drugs, and the like; antiparasitic compounds such as ivermectin;

antiviral compounds such as acyclovir and interferon;

analgesics such as aspirin, salicylic acid, diflunisal, morphine and its salts and the like;

antiseptic substances such as cetylpyridinium chloride, benzalkonium chloride, chlorhexidine and the like;

antimycotic substances such as cetyltrimethylammonium bromide and the like;

antifungals such as polyoxyethylene nonylphenols, alkylaryl sulfonates, miconazole nitrate, metronidazole, trimethoprim and the like;

antiprotozoals such as chloramphenicol, sulfamethoxazole and the like;

local anesthetics such as salts of procaine, benzocaine, lidocain, procain, bupivacaine, tetracain, xylocaine, mepivacaine and their salts and the like;

antiasthma drugs such as adrenaline, ephedrine, epinephrine, aminophylline, theophylline and the like;

urinary tract disinfectives such as trimethroprim, nitrofurantoin, norfloxacin and the like;

anticoagulants such as heparin and its salts, such as calcium and sodium heparin, bishydroxycoumarin and the like;

anticonvulsants such as diazepam, sodium phenytoin and the like;

antidiabetics such as insulin, tolbutamide, somatostatin and its analogs, tolazanide, acetohexamide, chlorpropamide and the like;

antihypertensive such as methyldopa, hydralazine, clonidine, chlorothiazide, timolol, propanolol, metroprolol, prazosin hydrochloride, furosemide and the like;

muscle relaxants such as succinylcholine chloride, danbrolene, cyclobenzaprine, methocarbamol, diazepam and the like;

vitamins such as $B_6$, $B_{12}$ and C and the like;

diagnostic aids such as sodium oleate and the like (pancreatic function) and the like;

contrast media such as $BaSO_4$, iohexol and other iodine-containing substances and the like (x-ray), iron(II,III)oxide particles and other ferromagnetic materials (magnetic resonance imaging).

EXAMPLES

Nonionic cellulose derivatives and ionic surfactants are mixed in water to give a relatively easily flowing solution at room temperature. The surfactants could either be negatively or positively charged. If such a system, containing appropriate types and amounts of cellulose ether and cosolutes, is heated to 30°–42° C., in particular 37° C., its rheological properties will be drastically changed, leading to the reversible formation of a stiff and transparent gel. Representative systems are described below.

It is also demonstrated that nonionic cellulose derivatives having a cloud point over 35° C. do not form a gel at body temperature.

In the following examples the viscosity values, n, refer to steady-flow viscosity measured on a Bohlin VOR rheometer Bohlin Reologi, Lund, Sweden), measuring system: C 25; torque element: 21.6 g cm (or equivalent), at the stated shear rate.

The cloud point, (CP; flocculation or phase separation temperature) has been determined for a 1.0 wt % solution of the cellulose ether in water, heated at a rate of 10° C./min, on a Mettler FP5+FP51 spectrophotometer. In the following tests and examples all percentages refer to percent by weight.

The tests in the examples below were performed with ethyl hydroxyethyl cellulose, EHEC, of different qualities, i.e.:

|  | $DS_{ethyl}$ | $MS_{EO}$ | CP, °C. | η, mPas |
|---|---|---|---|---|
| EHEC A | 1.7 | 1.0 | 34.0 | 42 |
| EHEC B | 1.9 | 1.3 | 34.4 | 89 |
| EHEC Bermocoll ® CST 103 Batch 1 | 1.5 | 0.7 | 35.9 | 40 |
| EHEC Bermocoll ® CST 103 Batch 2 | 1.5 | 0.7 | 36.8 | 46 |
| EHEC Bermocoll ® E230 G | 0.8 | 0.8 | 63 | 40 |

Viscosity values (η) were measured on 1% aqueous solutions at a shear rate of 7.31 s$^{-1}$ at 20° C.;

Example 1

| Composition | Concentration, % |
|---|---|
| Ethyl hydroxyethyl cellulose (EHEC A) | 0.75 |
| Tetradecyl betainate (TDB; tetradecyloxycarbonyl-N,N,N,-trimethylmethanaminium chloride (Berol Nobel)) | 0.15 |
| Water, deionized | 99.1 |

Viscosity at different temperatures

| Temperature*, °C. | 20 | 25 | 30 | 35 | 37 | 40 |
|---|---|---|---|---|---|---|
| η**, mPas | 130 | 1,100 | 6,600 | 72,000 | 46,000 | 27,000 |

*dT/dt = 2° C./min
**Shear rate 0.233 s$^{-1}$

Viscosity at different concentrations of surfactant

| | η*, mPas | |
|---|---|---|
| TDB conc., % | 20° C. | 37° C.** |
| 0 | 25 | |
| 0.10 | 74 | 73,000 |
| 0.12 | 93 | 54,000 |
| 0.15 | 130 | 15,000 |

*Shear rate 0.233 s$^{-1}$
**Thermal equilibrium time 8 min

Example 2

| Composition | Concentration, % |
|---|---|
| Ethyl hydroxyethyl cellulose (EHEC B) | 1.0 |
| Sodium dodecyl sulphate (SDS) | 0.09 |
| Water, deionized | 98.91 |

Viscosity at different temperatures

| Temperature °C. | 20.1 | 25.3 | 30.4 | 33.3 | 35.0 | 36.8 | 37.5 | 38.3 | 39.0 | 39.8 | 42.3 | 42.3 |
|---|---|---|---|---|---|---|---|---|---|---|---|---|
| η**, Pas | 0.32 | 0.47 | 1.21 | 2.70 | 5.56 | 15.5 | 39.2 | 66.0 | 90.4 | 114 | 130 | 111 |

*dT/dt = 1° C./min
**Shear rate 0.216 s$^{-1}$

Viscosity at different concentrations of surfactant

| | η*, mPas | |
|---|---|---|
| SDS conc., % | 20° C. | 37° C. |
| 0.09 | 147 | 108,000 |
| 0.12 | 500 | 86,000 |
| 0.14 | 1,290 | 36,000 |

*Shear rate 0.216 s$^{-1}$
**Thermal equilibrium time 8 min

Example 3

| Composition | Concentration, % |
|---|---|
| Ethyl hydroxyethyl cellulose (EHEC B) | 1.0 |

| | |
|---|---|
| Cetyltrimethylammonium bromide (CTAB) | 0.15–0.22 |
| Water, deionized | 99.85–98.78 |

Viscosity at different concentrations of surfactant

| | $\eta^*$, mPas | |
|---|---|---|
| CTAB conc., % | 20° C. | 37° C. |
| 0.15 | 194 | 10,500 |
| 0.18 | 270 | 8,200 |
| 0.22 | 296 | 8,200 |

*Shear rate 0.216 $s^{-1}$
**Thermal equilibrium time 8 min

Example 4

| Composition | Concentration, % |
|---|---|
| Ethyl hydroxyethyl cellulose (EHEC B) | 0.85 |
| Sodium oleate | 0.05 |
| Water, deionized | 99.1 |

Viscosity at different temperatures

| Temperature*, °C. | 20.2 | 24.3 | 30.2 | 31.8 | 33.3 | 34.7 | 36.2 | 37.4 | 41.1 | 44.3 |
|---|---|---|---|---|---|---|---|---|---|---|
| $\eta^{**}$, Pas | <0.3 | <0.3 | <0.3 | <0.3 | 0.4 | 0.7 | 1.3 | 3.0 | 14.6 | 71.9 |

*dT/dt = 1° C./min
**Shear rate 0.233 $s^{-1}$

COMPARATIVE EXAMPLES

Example 5

| Composition | Concentration, % |
|---|---|
| Ethyl hydroxyethyl cellulose (Bermocoll® CST 103 Batch 1) | 0.85 |
| Sodium oleate | 0.05 |
| Water, deionized | 99.1 |

Viscosity at different temperatures

| Temperature*, °C. | 19.9 | 24.3 | 30.3 | 32.3 | 34.2 | 36.1 | 37.8 | 39.3 | 42.4 | 44.4 |
|---|---|---|---|---|---|---|---|---|---|---|
| $\eta^{**}$, Pas | <0.3 | <0.3 | <0.3 | <0.3 | <0.3 | 0.4 | 0.5 | 0.8 | 2.0 | 14.1 |

*dT/dt = 1° C./min
**Shear rate 0.233 $s^{-1}$

Example 6

| Composition | Concentration, % |
|---|---|
| Ethyl hydroxyethyl cellulose (Bermocoll® E230 G) | 0.85 |
| Sodium oleate | 0.05 |
| Water, deionized | 99.1 |

Viscosity at different temperatures

| Temperature*, °C. | 20.1 | 24.3 | 30.2 | 31.9 | 33.4 | 34.9 | 36.2 | 37.7 | 41.5 | 44.3 |
|---|---|---|---|---|---|---|---|---|---|---|
| $\eta^{**}$, Pas | 0.3 | <0.3 | <0.3 | <0.3 | <0.3 | <0.3 | <0.3 | <0.3 | <0.3 | <0.3 |

*dT/dt = 1° C./min
**Shear rate 0.233 $s^{-1}$

These examples show that compositions based on ethyl hydroxyethyl celluloses with a CP higher than 35° C. do not form a gel at body temperature.

When EHEC Bermocoll® CST 103, Batches 1 and 2, respectively, were combined with SDS and water, as described in Example 2, no gelling occurred after heating as confirmed by ocular inspection.

TEST ON GEL FORMATION IN GASTRIC JUICE IN VITRO

The gel forming ability in vitro in simulated gastric juice has been tested for a composition according to the invention, a solution of 0.85% EHEC B+2.6% glycerol+0.087% SDS in water.

The gastric juice solution is prepared according the recipe in USP XXII: pepsin (3.2 g), dissolved in hydrochloric acid (7.0 ml), and sodium chloride (2.0 g) are mixed and dissolved in 1000 ml water. 25 ml of the solution is transferred to a container immersed in a thermostat bath (37° C). 5 ml of the polymer solution/dispersion to be tested is then gently added to the gastric juice solution without stirring and the system is then visually examined.

A gel is formed and there is no appreciable change in size after 1 h. The gel has a somewhat milky appearance due to the high ionic strength of the gastric juice which leads to partial phase separation on the surface of the gel lump. Cooling to room temperature leads to a complete mixing and disappearance of the gel.

TEST ON GEL MAINTENANCE IN INTESTINAL JUICE IN VITRO

A simulated intestinal juice was prepared as follows in accordance with USP XXII: $KH_2PO_4$ (6.8 g) is dissolved in deionized water (250 ml). 0.2M NaOH (190 ml) and deionized water (400 ml) are then added and mixed. To this solution pankreatin (10.0 g) is added and the pH is adjusted to 7.5±0.1 with 0.2M NaOH. The final volume (1000 ml) is adjusted with water.

The gel formed in the gastric juice system above was after 2 h transferred to the simulated intestinal juice, heated to 37° C. The gel was maintained in the new environment for at least 22 h. The volume of the gel lump was only reduced by ca 50%.

PHARMACEUTICAL COMPOSITIONS

A nonionic cellulose ether (EHEC) and ionic surfactants are mixed in water to give a relatively easily flowing solution at room temperature. A biologically, that is pharmacologically, active component, e.g. a drug, which could either be hydrophilic (charged or noncharged), hydrophobic or amphiphilic in nature, is added to the mixture. Alternatively, the surfactant could be replaced by the drug if the latter is strongly amphiphilic in character. If such a system, containing appropriate types and amounts of EHEC and cosolutes, is heated to 30°–42° C., in particular to 37° C., its rheological properties are drastically changed, leading to the (reversible) formation of a stiff and transparent gel. The EHEC polymer without surfactant is also an excellent excipient in pharmaceutical formulations, owing to its thickening, emulsion stabilizing, as well as adhesive properties.

| Oral composition | |
|---|---|
| Antiasthmatic composition | Concentration, % |
| EHEC of medical grade | 1.0 |
| Sodium dodecyl sulphate | 0.087 |
| Theofylline | 0.080 |
| Water, purified | 98.8 |
| Buccal composition I | |
| Anti-caries composition | Concentration, % |
| EHEC of medical grade | 0.50 |
| Sodium dodecyl sulphate | 0.174 |
| Sodium fluoride | 0.05 |
| Water, purified | 99.3 |

The NaF concentration could range from 0.05 to 0.5%. At most the SDS concentration is 0.35% (for 0.75% EHEC). An increase in SDS content decreases the ability of the teeth to adsorb F$^-$ and therefore a low SDS content is desirable. Compared to toothpastes the SDS content required in these EHEC systems is very small (normally the SDS content varies between 0.5 and 2%).

| Buccal composition II | |
|---|---|
| Antifungoid mouth wash | Concentration, % |
| EHEC of medical grade | 0.85 |
| Hydroxypropyl-β-cyclodextrin (Aldrich) | 5.0 |
| Hydrocortisone | 0.6 |
| Water, purified | 93.6 |

The composition is a clear, low-viscous solution with a high drug load which is easy to apply. Hydrocortisone is normally administered as an ointment or a cream—administration forms which are difficult to apply in the mouth and which are also unpleasant to use. The most important advantage of this formulation is that it adheres to the mucous membrane, has a high water holding capacity and thus relieves xerostomia which is the usual cause of fungoid growth.

| Dermal composition I | |
|---|---|
| Analgetic composition | Concentration, % |
| EHEC of medical grade | 0.75 |
| Sodium dodecyl sulphate | 0.087 |
| Salicylic acid | 0.1 |
| Water, purified | 99.1 |
| Dermal composition II | |
| Antiseptic composition | Concentration, % |
| EHEC of medical grade | 1.0 |
| Benzalkonium chloride | 0.4 |
| Water, purified | 98.6 |
| Dermal composition III | |
| Antimycotic composition | Concentration, % |
| EHEC of medical grade | 0.75 |
| Cetylpyridinium chloride | 0.1 |
| Water, purified | 99.15 |

Ocular composition

Three different solutions were prepared from the following constituents: EHEC of medical grade, tetradecyl betainate (TDB), timolol hydrogen maleate (TM; Sigma) and purified water.

| Antiglaucoma composition (%) | | | | |
|---|---|---|---|---|
| System | EHEC | TDB | TM | Water |
| 0.34% TM (aq) | — | — | 0.34 | 99.66 |
| 1 | 1.0 | 0.475 | 0.34 | 98.185 |
| 2 | 2.0 | 0.930 | 0.34 | 96.73 |
| Nasal composition I | | | | |
| Nasal decongestant composition | | | | Concentration, % |
| EHEC of medical grade | | | | 1.10 |
| Cetyltrimethylammonium bromide | | | | 0.109 |
| Oxymethazoline-HCl | | | | 0.018 |
| Water, purified | | | | 98.9 |
| Nasal composition II | | | | |
| Haemostatic composition | | | | Concentration, % |
| EHEC of medical grade | | | | 1.0 |
| Sodium dodecyl sulphate | | | | 0.087 |
| Tranexamic acid | | | | 10.0 |
| Water, purified | | | | 89.9 |
| Nasal composition III | | | | |
| Antidiabetic composition | | | | μl |
| 1% aqueous EHEC solution with 0.087% sodium dodecyl sulphate | | | | 800 |
| Insulin (Actrapid ® Human) | | | | 100 |
| Purified water | | | | 100 |
| Rectal Composition I | | | | |
| Anti-inflammatory composition | | | | Concentraton, % |
| EHEC of medical grade | | | | 1.0 |
| SDS | | | | 0.087 |
| Prednisolone | | | | 0.1 |
| Water | | | | 98.8 |
| Rectal Composition II | | | | |
| Anti-inflammatory composition | | | | Concentration, % |
| EHEC of medical grade | | | | 1.0 |
| SDS | | | | 0.087 |
| Budesonide | | | | 0.01 |
| Water | | | | 98.9 |

Surprisingly, both water-insoluble (budesonide) and very slightly soluble (prednisolon) drug substances can be successfully incorporated in the carrier system without affecting the thermogelling effect as judged from visual inspection after heating the suspension to 37° C. Furthermore, and most importantly, the suspensions are stable during long periods of storage; e.g. Rectal composition II (budesonide) was stored for 8 months at room temperature without any sediments being observed on the bottom of the test tube.

TEST ON RELEASE IN VITRO

Test of the ocular composition

In order to demonstrate the ability to sustain the in vitro release of timolol maleate from the gel-forming EHEC-charged surfactant system, the Ocular composition, described above was studied in a USP paddle apparatus (Dissolutest, Prolabo), connected to a spectrophotometer (Lambda 2, Perkin-Elmer).

Samples of the three ocular solutions were poured into plexiglass cups with a 4.0 ml cylindrical bore (diffusion surface 21.24 cm$^2$). The cups were covered with nylon bolting cloth (mesh size 80 DIN) to keep the gel samples in place during the test. Cups filled with sample solution were incubated at 40° C. for 15 min immediately before the test. This induced gel formation in systems 1 and 2. The test was started when the cups had been immersed in the medium in the apparatus and the paddles had started to rotate.

The release of timolol maleate was detected spectrophotometrically. The following test parameters were used in the test
Sample volume: 4.0 g (filled cups)
Medium: 500 ml 8.15 mmolar NaCl(aq), isotonic with 0.34% TM
Temperature: 37.0°±0.3° C.
Paddle speed: 20 rpm
Wavelength: 295.0 nm, UV lamp
Background corr.: before every measurement cycle
Spect. reference: pure medium
Pump speed: 99 (maximal speed for the peristaltic pump, Ismatech IPN-16, Labinette)

The test results, which are plotted in FIG. 1, clearly reveal the difference in release rate of timolol from the 0.34% aqueous reference solution and the two gelled EHEC-ionic surfactant systems.

Test of the Nasal composition III

In order to demonstrate the in vitro release profile of insulin from the carrier system of the invention, the following diffusion model was used.

To the donor compartment of a diffusion apparatus comprising a donor compartment, a receiving compartment, a membrane, and a sampling site, thermostated at 37° C., was added 1 ml of the composition. Sampling from the receiving compartment was made after 3, 5, 10, 15, 30, 60, 120 and 180 min. The insulin content was analysed according to the Folin-Lowry method.

Figure 2:
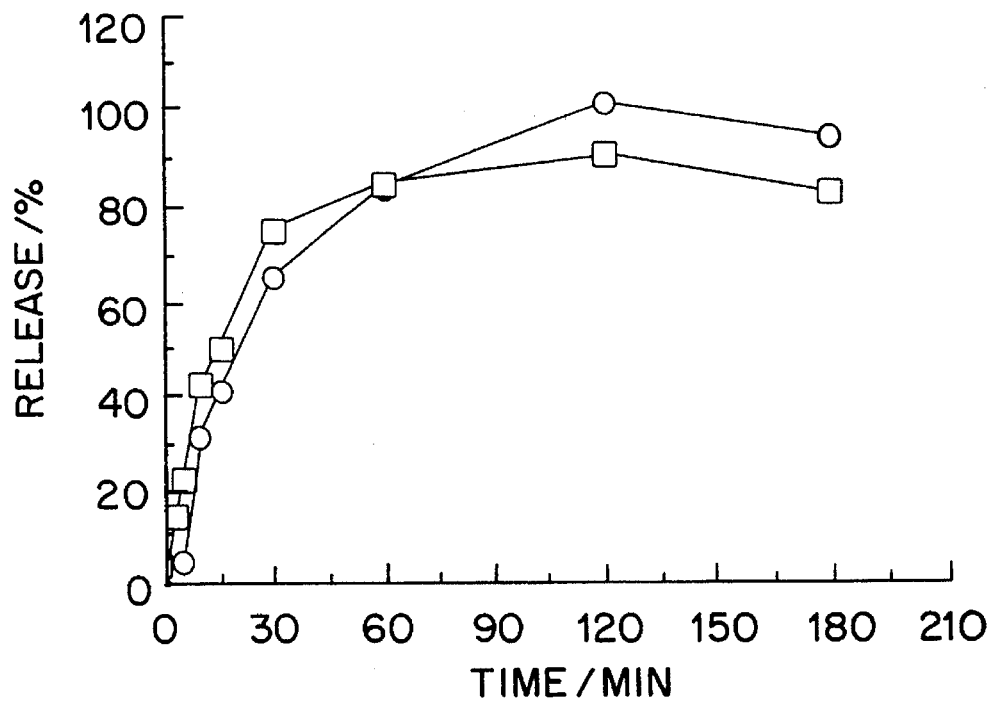
FIG. 2 is a graph demonstrating in vitro release profile of insulin from a carrier system of the present invention.

The test results with the Nasal composition III (circles) as well as Carbopol® 934P, crosslinked poly(acrylic acid) (squares) are given in FIG. 2.

TESTS IN VIVO

Release of insulin in rat

The efficiency of a carrier composition of the invention was tested by nasal administration of insulin to anaesthetised rats, in which the arteria carotis had been catheterized and trachea tubings inserted, and subsequent measurement of the blood glucose level.

The Nasal composition III, as described above, as well as a reference system based on 0.5% Carbopol® 934P in water, were administrated via the nostril, through a polyethylene catheter and an automatic pipette in a dose of 1 IU insulin/kg. Carbopol, a crosslinked poly(acrylic acid), is a viscosity-increasing polymer with bioadhesive properties which is commonly used as a carrier in drug delivery systems. The insulin content both in the composition of the invention and in the reference solution was 10 IU/ml.

Blood samples were collected after 3, 5, 10, 15, 30, 60, 120, 180 and 240 minutes and the glucose levels were enzymatically assayed on a Beckman DRISTAT.

Figure 3:
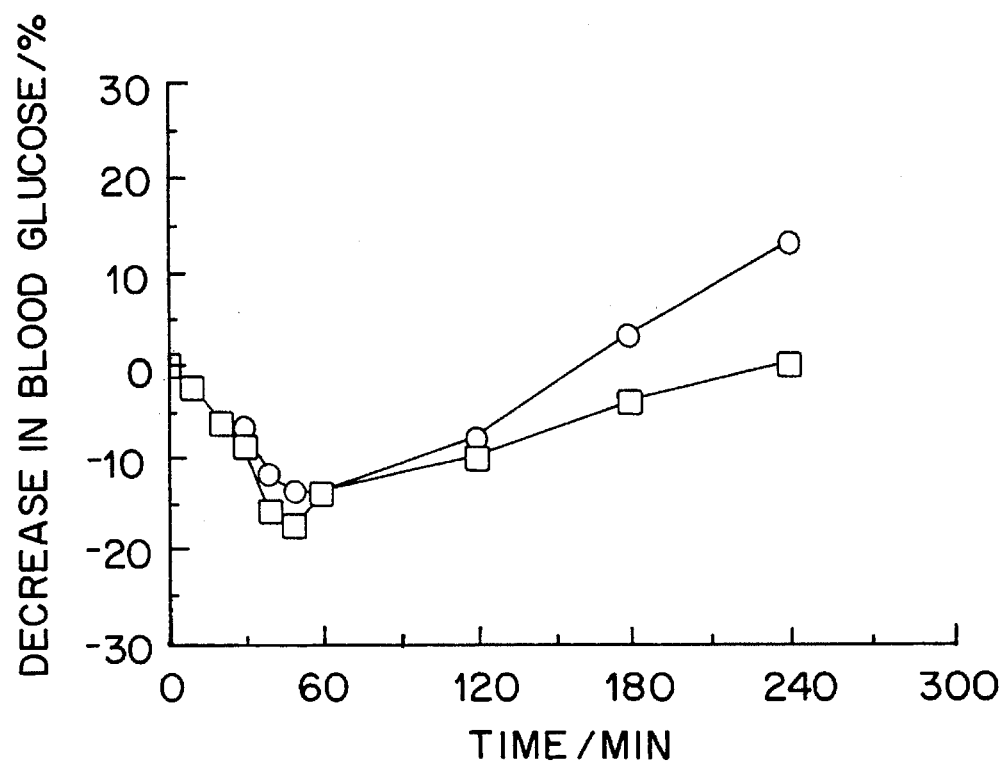
FIG. 3 is a graph demonstrating in vivo release profile of insulin from a carrier system of the present invention.

The results are given in FIG. 3 (Circles: Nasal composition III; Squares: Carbopol® solution). The test in vitro as well as the test in vivo both show that the EHEC-SDS system is equivalent to the Carbopol system as to release and delivery of insulin.

Effect on xerostomia in man

Xerostomia, mouth dryness, implies a decrease of saliva secretion that may cause an impairment of the mucous barrier protective properties. Xerostomia may have many causes. For relieving some of the problems related to xerostomia many patients use saliva substitutes containing bioadhesive polymers, e.g. sodium carboxymethyl cellulose and mucin.

A new technique has been developed for evaluating oral mucosal dryness. An instrument comprising a probe measures the mucosal slide friction and the lubrication properties of different bioadhesive formulations (V. Henricson, A. Svensson, H. Olsson, T. Axell: Evaluation of a new device for measuring oral mucosal surface friction, 1990, Scand. J. Dental Res. 98, 529–536).

The lubrication properties of saliva substitutes based on mucin, sodium carboxymethyl cellulose and EHEC and of water have been evaluated by using this technique.

Six patients with xerostomia (average age 73 years) were selected for the study. All of them suffered from xerostomia and the condition was related to salivary gland diseases. Three suffered from documented Sjögren's syndrome, fulfilling the Copenhagen criteria, and the other three showed unspecific sialoadenitis at biopsy. All six patients showed a mixed salivary flow rate below 1.5 ml/15 min at rest. No one had any clinically visible mucosal lesions. None of the patients used drugs on a regular basis or smoked tobacco.

The patients were asked not to drink or eat anything during the last hour before the start of the experiment. Before rinsing, a basal friction value of lip mucosa was registered with the probe. Thereafter, the patients rinsed the mouth during one minute with 15 ml test solution. The friction value of the lip was then measured with the probe approximately every fifth minute until the basal value was re-established. The effect was defined as the time in min which elapsed from the end of the rinsing and until the basal value was recorded.

| Results | |
| --- | --- |
| Saliva substitute | Mean value, min |
| Saliva Orthana ®* | 11 |
| 1.0% sodium carboxymethyl cellulose | 16 |
| 1.0% EHEC | 15 |

-continued

| Results | |
|---|---|
| Saliva substitute | Mean value, min |
| 0.75% EHEC + 0.10% CTAB | 19 |
| 0.75% EHEC + 0.115% SDS | 11 |
| Pure Water | 6 |

*Saliva substitute containing 3.5% mucin, from A/S Orthana Kemisk Fabrik, Kastrup, DK?

All saliva substitutes showed almost the same lubrication effect on the oral mucosal friction. This effect lasted about twice as long as for water. This means that the EHEC compositions in these studies have lubrication and bioadhesive properties that are equal to that of the well-known bioadhesive polymers mucin and sodium carboxymethyl cellulose.

MUCOADHESION STUDIES IN VITRO

The mucoadhesive properties of different carrier compositions were investigated by comparison of the mean peak detachment forces recorded when samples were separated from a model mucus gel (I. W. Kellaway in Bioadhesion and Future Trends, H. E. Junginger and R. Gurny, Eds, Wissenschaftliche Verlags GmbH, Stuttgart 1990).

The tests were performed with the following EHEC qualities:

| | CP, °C. | $MS_{EO}$ | $DS_{ethyl}$ |
|---|---|---|---|
| EHEC C | 37.0 | 0.9 | 1.4 |
| EHEC D | 32.0 | 1.1 | 1.7 |

Mucoadhesion measurement

The mucoadhesion testing was performed as follows. The mucus gel was held on an evacuated probe. A lower cell held the test composition and was sealed to allow the chamber beneath to be evacuated. The cell was placed on a balance pan and tared. The probe was lowered onto the composition at a constant rate (3.27 mm/min) to a specified loading (10 g), the formulation was then separated from the mucus gel (3.27 mm/min). This was repeated five times for each sample of mucus and composition. Data output was stored in a computer for subsequent analysis. To facilitate testing at the specified temperatures the balance was insulated and heated with an electrical element fitted with a rheostat.

Model mucus gel

Purified porcine gastric mucin (BDH) 0.2 g was hydrated with pH 7.4 buffer (0.8 ml). At this concentration the visco-elastic properties of the gel approximated those of porcine gastric mucin purified in-house. Stock batches were made up so that each composition was tested with mucus from the same batch. 0.1 g samples of the mucus gel were weighed onto an ultra filtration membrane (22 mm diameter), and brought to experimental temperature in the balance. The samples were placed on the probe, held by vacuum and spread to give a uniform surface.

Test formulations

Test compositions according to below were refrigerated (<8° C.), the sample bottles were vigorously shaken and brought to room temperature prior to use. For each test 400 μl of the composition was carefully pipetted to avoid air entrapment on to an ultrafiltration membrane on the cell and held in place by vacuum. The cell was then brought to experimental temperature in the balance. The nature of the compositions allowed them to flow and cover the membrane with a thin even layer.

Compositions 1. 1.25% sodium carboxymethyl cellulose (Cekol® MVG; Billerud, Sweden)
2. 1.25% EHEC C
3. 1.25% EHEC C+0.115% SDS
4. 1.25% EHEC D
5. 1.25% EHEC D+0.115% SDS

Results

Results are summarized in the following table showing the mean peak detachment forces (± standard deviation) required for separating the compositions 1–5 from the mucus gel at 37° C.

| Composition | 1 | 2 | 3 | 4 | 5 |
|---|---|---|---|---|---|
| Run 1 | 8.06 ± 0.74 | 9.30 ± 1.54 | 9.78 ± 2.00 | 7.72 ± 0.59 | 10.45 ± 1.52 |
| Run 2 | 8.82 ± 0.46 | 8.61 ± 1.74 | 8.24 ± 0.32 | 7.77 ± 0.65 | 9.43 ± 0.59 |

Conclusions

All test compositions were mucoadhesive, however statistical analysis of the mean peak detachment forces established that significant differences existed between the compositions. Duncans multiple comparison test indicated that composition 5 required a significantly greater force for detachment than composition 4. In addition the performance of composition 5 appeared to be superior to that of 1, 2 and 3 although statistically there were no proven differences.

These studies show that both EHEC and the carrier system of the invention are bio(muco)adhesive. It could also be concluded that the addition of a charged surfactant improves the bioadhesive properties of the cellulose ether.

We claim:

1. A carrier composition which is a liquid at or below room temperature and forms a high viscosity layer or gel at body temperature, characterized in comprising a water-soluble, nonionic cellulose ether having a cloud point not higher than 40° C., a charged surfactant and optional additives in water wherein said optional additives are selected from the group consisting of flavoring agents, colorants, preservatives, isotonic agents and mixtures thereof, and in that the combined concentration of the water-soluble, nonionic cellulose ether and the surfactant is below 3% by weight, and wherein the remainder of the composition is water and said optional additives.

2. A carrier composition according to claim 1, wherein the water-soluble, nonionic cellulose ether has a cloud point not higher than 35° C.

3. A carrier composition according to claim 1, wherein the water-soluble nonionic cellulose ether is an alkyl hydroxyalkyl cellulose, the alkyl groups of which have from 1 to 4 carbon atoms.

4. A carrier composition according to claim 1, wherein the water-soluble nonionic cellulose ether is ethyl hydroxyethyl cellulose with a $DS_{ethyl}$ value of 1.2–2.5, a $MS_{EO}$ value of 0.5–1.5 and a cloud point of 30°–35° C.

5. A carrier composition according to claim 1, wherein the charged surfactant has a positively or negatively charged headgroup and a hydrocarbon chain of from 10 to 20.

6. A carrier composition according to claim 1, wherein the charged surfactant comprises a prodrug.

7. A carrier composition according to claim 1 for oral or local administration of a drug and/or a prodrug to the skin, the mucous membrane, the eye or a body cavity.

8. A pharmaceutical composition which is liquid at and below room temperature and forms a high viscosity layer or gel at body temperature, characterized in comprising a pharmacologically active substance in combination with a carrier composition according to claim 6.

9. A pharmaceutical composition which is liquid at and below room temperature and forms a high viscosity layer or gel at body temperature, characterized in comprising a water-soluble, nonionic cellulose ether having a cloud point not higher than 40° C., an amphiphilic drug and optional additives in water, wherein said optional additives are selected from the group consisting of flavoring agents, colorants, preservatives, isotonic agents and mixtures thereof, and wherein the combined concentration of the water-soluble, nonionic cellulose ether and the surfactant is below 3% by weight, and wherein the remainder of the composition is water and said optional additives.

10. A carrier composition according to claim 2, wherein the water-soluble nonionic cellulose ether is an alkyl hydroxyalkyl cellulose, the alkyl groups of which have from 1 to 4 carbon atoms.

11. A carrier composition according to claim 2, wherein the water-soluble nonionic cellulose ether is ethyl hydroxyethyl cellulose with a $DS_{ethyl}$ value of 1.2–2.5, a $MS_{EO}$ value of 0.5–1.5 and a cloud point of 30°–35° C.

12. A carrier composition according to claim 2, wherein the charged surfactant has a positively or negatively charged headgroup and a hydrocarbon chain of from 10 to 20 carbon atoms.

13. A carrier composition according to claim 2, wherein the charged surfactant comprises a prodrug.

14. A carrier composition according to claim 2 for oral or local administration of a drug and/or a prodrug to the skin, the mucous membrane, the eye or a body cavity.

15. A pharmaceutical composition which is liquid at and below room temperature and forms a high viscosity layer or gel at body temperature, characterized in comprising a pharmacologically active substance in combination with a carrier composition according to claim 2.

16. A carrier composition according to claim 1 wherein the concentration of the water-soluble, nonionic cellulose ether and surfactant is 0.5–1.5% by weight.

17. A carrier composition according to claim 5 wherein said hydrocarbon chain has 12 to 18 carbon atoms.

18. The composition of claim 1 wherein said optional additives include a nonionic, low-molecular weight compound in an effective isotonic concentration.

19. The composition of claim 1 wherein said low-molecular weight compound is selected from the group consisting of sucrose, glucose and glycerol.

20. The composition of claim 1 wherein said optional additives comprise a member selected from the group consisting of flavoring agent, colorant and preservative.

* * * * *